(12) United States Patent
Maaloul et al.

(10) Patent No.: US 10,827,990 B2
(45) Date of Patent: Nov. 10, 2020

(54) DEVICE FOR SIGNALING THE STATUS OF AN IN-OUTSIDE RADIO-ELECTRIC EMITTING APPARATUS, AND IN PARTICULAR AN APPARATUS PROVIDED WITH AN X-RAY TUBE

(71) Applicant: BIOMEDIQA, Villeneuve d'ascq (FR)

(72) Inventors: Fouad Maaloul, Marq en Baroeul (FR); Laura Guerin, Lille (FR)

(73) Assignee: BIOMEDIQA (FR)

( * ) Notice: Subject to any disclaimer, the term of this patent is extended or adjusted under 35 U.S.C. 154(b) by 281 days.

(21) Appl. No.: 15/574,973

(22) PCT Filed: May 9, 2016

(86) PCT No.: PCT/FR2016/051081
§ 371 (c)(1),
(2) Date: Nov. 17, 2017

(87) PCT Pub. No.: WO2016/185112
PCT Pub. Date: Nov. 24, 2016

(65) Prior Publication Data
US 2018/0132802 A1    May 17, 2018

(30) Foreign Application Priority Data

May 19, 2015   (FR) ...................... 15 54474

(51) Int. Cl.
*A61B 6/10*     (2006.01)
*A61B 6/00*     (2006.01)

(52) U.S. Cl.
CPC ............ *A61B 6/107* (2013.01); *A61B 6/4405* (2013.01); *A61B 6/46* (2013.01); *A61B 6/56* (2013.01)

(58) Field of Classification Search
None
See application file for complete search history.

(56) References Cited

U.S. PATENT DOCUMENTS

| | | | | |
|---|---|---|---|---|
| 4,797,907 A | * | 1/1989 | Anderton | ................. H05G 1/10 378/101 |
| 2014/0146946 A1 | * | 5/2014 | Newman | .............. A61B 6/4429 378/62 |
| 2014/0369459 A1 | * | 12/2014 | Foos | ........................ A61B 6/03 378/9 |

FOREIGN PATENT DOCUMENTS

| | | |
|---|---|---|
| CN | 202568292 U | 12/2012 |
| EP | 2 329 772 A1 | 6/2011 |
| JP | 2014-138667 A | 7/2014 |

OTHER PUBLICATIONS

International Search Report dated Jul. 25, 2016 in corresponding PCT International Application No. PCT/FR2016/051081.

(Continued)

*Primary Examiner* — Hoon K Song
(74) *Attorney, Agent, or Firm* — Ostrolenk Faber LLP

(57) ABSTRACT

A device for signalling into the environment the status of a radio transmission apparatus, and in particular of an apparatus provided with an X-ray tube, such that the signalling device includes:—a first part, capable of being connected at the power cable of the transmission apparatus, and includes means for measuring the current demand of the transmission apparatus, processing means for determining the status,—switched off, on standby, or in use—of the transmission apparatus depending on the current measurement and means for transmitting the detected status to a second part,—a second part including means for signalling the status of the transmission apparatus detected by the first part.

9 Claims, 2 Drawing Sheets

(56) References Cited

OTHER PUBLICATIONS

Written Opinion dated Jul. 25, 2016 in corresponding PCT International Application No. PCT/FR2016/051081.

* cited by examiner

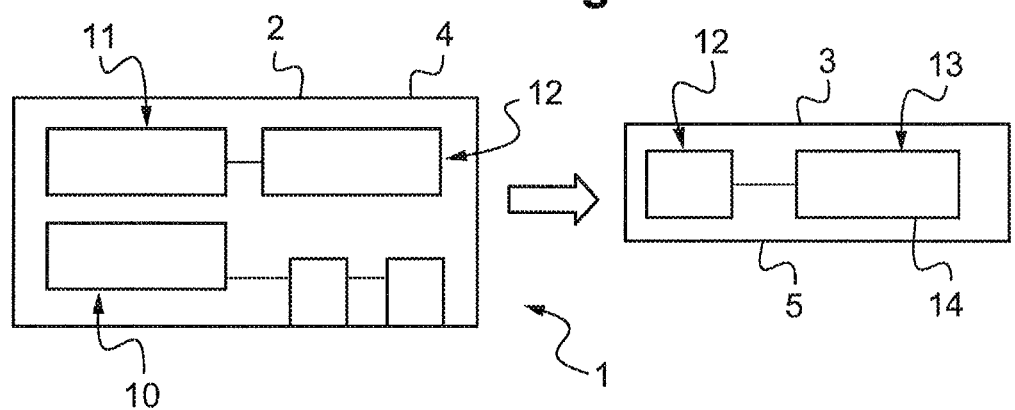
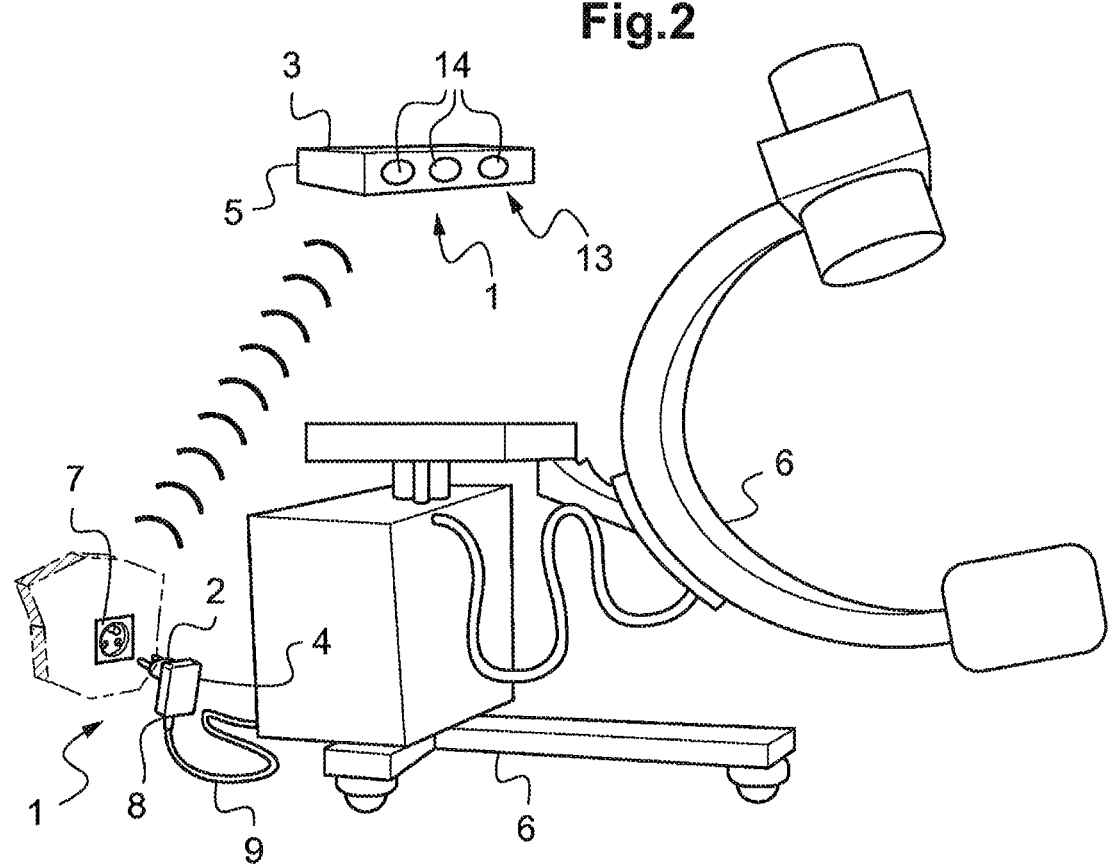

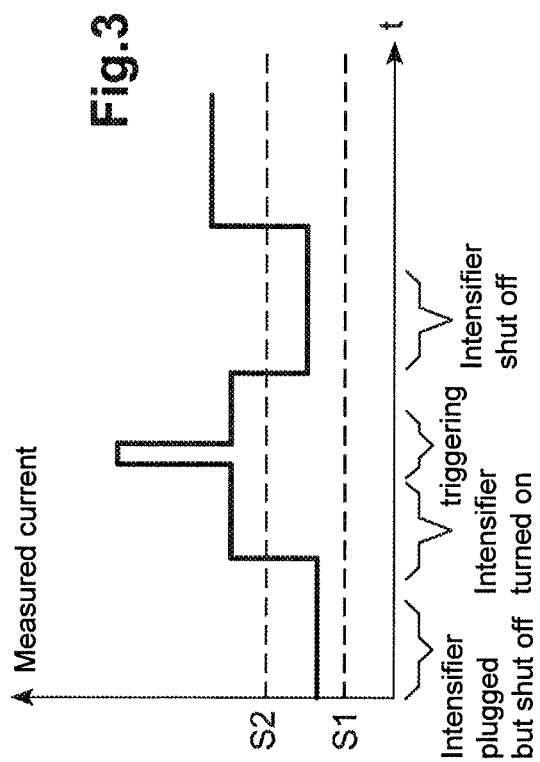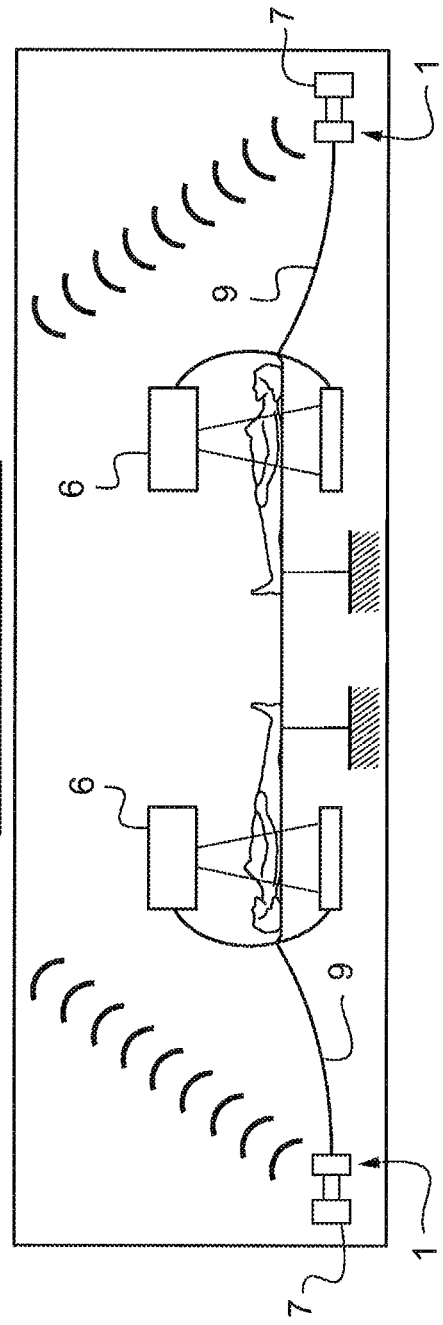

DEVICE FOR SIGNALING THE STATUS OF AN IN-OUTSIDE RADIO-ELECTRIC EMITTING APPARATUS, AND IN PARTICULAR AN APPARATUS PROVIDED WITH AN X-RAY TUBE

CROSS-REFERENCE TO RELATED APPLICATIONS

The present application is a 35 U.S.C. §§ 371 national phase conversion of PCT/FR2016/051081, filed May 9, 2016, which claims priority to French Patent Application No. 1554474, filed May 19, 2015, the contents of which are incorporated herein by reference. The PCT International Application was published in the French language.

TECHNICAL FIELD

The present invention concerns a device for signaling the status of an open-field radio-electric emitting apparatus, and in particular an apparatus provided with an X-ray tube. Particularly, the invention will be intended to equip mobile radiology apparatuses in hospitals or medical clinics.

Nonetheless, this usage is not restrictive, the device may in particular be associated more broadly to any type of radio-electric emitting apparatuses, whether stationary or mobile, whose emissions may cause safety problems and also on apparatuses equipping research laboratories or industrial plants.

PRIOR ART

In general, the hospitals have rooms dedicated to the use of radio-electric emitting apparatuses (set forth in the remainder of the present application by the expression «emitting apparatus»), they consist in particular of conventional radiology rooms or rooms for a scanner or for a gamma-camera.

In general, these rooms are equipped with stationary emitting apparatuses, and comprise means for protection against radiations. Among these protection means, there is generally provided a passive signage with particular inscriptions informing on the possible presence of ionizing radiations. Complementarily, these rooms also include luminous panels indicating whether the emitting apparatuses are activated or not. These rooms, dedicated to the reception of emitting apparatuses, require specific setup works and in particular cables laying between the luminous panels and the emitting apparatuses.

Although expensive and requiring a temporary closure of the rooms to equip, this solution is relatively satisfactory. Nonetheless, it is not suitable to mobile emitting apparatuses, indeed, there is a certain number of emitting apparatuses easily displaceable from one room to another, and often used in non-dedicated rooms and for example in operating rooms.

Among these emitting apparatuses, there are for example apparatuses provided with an X-ray tube or an image intensifier, the latter being displaced on need from an operating room to another.

It is understood that the use of emitting apparatuses in particular in non-dedicated rooms is problematic for the safety of the medical staff and of the patients since no signaling means informs on the risks of presence of radiations.

Of course, it is possible to indicate the incurred risk in all the rooms likely to receive emitting apparatuses, this being so, a constant signage in all rooms would either make the displacements difficult in the facility or would reduce the impact of the warning on the users, and more especially as these rooms are, in fine, subjected to radiations once in a while.

OBJECT OF THE INVENTION

A first aim of the present invention is to solve all or part of the technical problems related to the aforementioned prior art.

Another aim of the present invention is to propose a signaling device allowing signaling a radiation emission in the presence of an emitting apparatus in a room without requiring any particular arrangement of the room.

Another aim of the present invention is to propose a signaling device which may be adapted in a rapid and reliable manner to any type of stationary or mobile emitting apparatus.

Another aim of the present invention is to propose a signaling device in which the signage may be multiple and easily displaceable in order to be visible at all the points of access to the room.

Another aim of the present invention is to propose a signaling device allowing stopping the emitting apparatus in case of a risk of exposure, in particular in industrial plants.

SUMMARY OF THE INVENTION

The present invention concerns a device for signaling the status of an in-outside radio-electric emitting apparatus, and in particular an apparatus provided with an X-ray tube, and such that it comprises, according to the invention:
- a first portion, which may be connected at the level of the power cable of said emitting apparatus, and including means for measuring the current demand of said emitting apparatus, processing means allowing determining the status, shut-off, in standby or in use, of said emitting apparatus according to the current measurement and means for transmitting the detected status toward a second portion,
- a second portion including means for signaling the status of the emitting apparatus detected by said first portion.

DEFINITION

The term «in-outside radio-electric emitting apparatus» defines, in the context of the present invention, any apparatus generating radio-electric emissions out of its structure.

BRIEF DESCRIPTION OF THE FIGURES

The present invention will be better understood upon reading the description of a detailed embodiment with reference to the appended figures, provided as a non-limiting example, in which:

FIG. 1 represents a schematic embodiment of a signaling device in accordance with the invention, FIG. 2 represents an embodiment, in a perspective view of a signaling device placed on an emitting apparatus disposed in a room, FIG. 3 represents a graph of the current needs of an emitting apparatus according to its status, FIG. 4 represents an example of a set including two signaling devices with one central unit.

DETAILED DESCRIPTION OF THE INVENTION

The present invention aims to protect a device for signaling the status of an in-outside radio-electric emitting apparatus. Referring mainly to FIG. 1, there is represented, in a schematic form, an embodiment of this signaling device 1.

This signaling device 1 comprises two portions, namely a first portion 2 intended to be connected at the level of the power cable of an emitting apparatus and a second portion 3 intended to be positioned advantageously in front of an access of the room.

Preferably, as represented in FIG. 1, these two portions 2 and 3 are disposed in separate casings respectively 4 and 5, nonetheless, in another possible embodiment, all the elements of the device 1 will be combined into one single casing.

Referring to FIG. 2 representing the device 1 in operation on an apparatus 6, it can be seen that the first portion 2 is connected between the power supply source 7 of the apparatus and the plug 8 of the power cable 9.

The first portion 2 comprises means 10 for measuring the current demand of said emitting apparatus 6. Preferably, these measuring means 10 are made with a current clamp meter allowing measuring the intensity of the current required by the emitting apparatus. This being so, other current measuring devices, known to those skilled in the art, may also be considered instead of said current clamp meter.

The first portion 2 further includes processing means 11 allowing determining the status, shut-off, in standby or in use, of said emitting apparatus according to the current measurement performed by the measuring means 10.

Advantageously, the processing means 11 enable a self-learning of the low and high thresholds respectively during the first setting in standby mode and the first setting in operation of the emitting apparatus 6.

Referring to FIG. 3, there is represented a graph of the current needs of an emitting apparatus 6, for example an image intensifier, according to its status. For this image intensifier, there is a first need level when the apparatus 6 is in standby, then a second level corresponding to the same device in use.

It is important to note that in the present application, it is meant by standby, the state in which is the apparatus 6 when it is plugged but does not emit any radiation. Nonetheless, in this standby state, the apparatus 6 may execute commands or calculations. Furthermore, it is meant by the expression «in use», the state in which the apparatus 6 emits radiations.

The processing means 11 allow creating automatically a first low threshold S1 below the amount of current required for the standby mode, this threshold S1 allowing determining that the apparatus 6 is likely to emit a radiation and a second high threshold S2 representing a current value higher than S1 and lower than the minimum current demand of the apparatus in use. Advantageously, the value of the threshold S2 is proportional to that of S1. When exceeded increasingly, this second threshold S2 allows determining that the apparatus 6 is emitting or in preparation for emission.

In the preferred embodiment, the processing means therefore include at least two thresholds among which a first low threshold S1 is lower than the minimum current demand when the apparatus is in standby and a second high threshold S2 is lower than the minimum current demand of the apparatus in use. Nonetheless, in a simplified version, there is provided for the processing means 11 including only but one single threshold corresponding to S2.

Conversely, in another version, there is further provided a third threshold S3 corresponding to an intermediate value between S1 and S2 allowing distinguishing between the current demand in preparation for emission and the current demand during the emission. This threshold S3 allows signaling an additional status of the apparatus, namely a preparation for emission.

In another embodiment, the processing means 11 do not include any self-learning means but rather include a memory including pre-recorded fixed high and low thresholds according to the emitting apparatuses to which corresponds the signaling device 1.

The first portion 2 further includes means 12 for transmitting the detected status of the apparatus 6 toward the second portion 3.

In the illustrated embodiment, the first and second portions 2 and 3 are housed in independent casings 4 and 5, and said transmission means 12 including a wireless link.

This feature is particularly interesting since it allows placing the second portion 2 including signaling means 13 in a location visible from the accesses of the room without any cables laying constraint. In this respect, the casing 5 allows housing a battery allowing ensuring the autonomy of the second portion 2.

In a manner known per se, the wireless transmission means 12 are made from a radio-electric emitter/receiver and for example of the Bluetooth type, or of the NFC type. Optionally, the link between the two portions 2 and 3 may be encoded so as to avoid any risk of interference and/or of pairing error for example between different signaling devices 1 disposed in geographically proximate rooms.

Preferably, the signaling means 13 are luminous and/or audible. According to an advantageous first embodiment, there is provided at the level of the second portion 3 at least one lamp 14 allowing obtaining a colored signal coding. According to another embodiment, the second portion 3 comprises a display allowing displaying texts corresponding in particular to the status of the apparatus 6 identified and transmitted by the first portion 2.

Referring this time to FIG. 4, there is represented a room equipped with several emitting apparatuses 6, each connected to a signaling device 1. In this configuration, there is provided a central display unit 15 allowing displaying one single signal or message according to the status of each emitting apparatus 6.

Thus, the central unit 15 displays the signal corresponding to the highest status degree reached by any of the emitting apparatuses measured in the room, the highest status being of course an apparatus 6 in use.

Preferably, the central unit 15 is made with a second portion 3 paired with all the first portions 2 of the signaling devices 1 present in the room.

In one variant, the central unit 15 may also separately display the status of each signaling device 1 to which it is connected with an identification of the code or the name of each device 1.

Thus, the present invention also aims to protect a set including a central unit allowing receiving the signal emitted by at least one first portion 2 of the signaling device 1 and allowing collecting the status data relating to several signaling devices.

In one variant, there is provided for the device 1 comprising, at the level of the processing means 11, means for monitoring the number of usage hours of the emitting apparatuses either separately or per areas over a determined time period. For this purpose, the usage history of each apparatus is transmitted to a central unit which collects all the data relating to the different concerned devices. Afterwards, these data are processed in order to carry out risk studies and to determine areas with variable risk or still to schedule operations of maintenance of the emitting apparatuses.

Of course, other features of the invention would also be considered without departing from the scope of the invention defined by the claims hereinafter.

As example, in one variant, the signaling device 1 comprises the first portion including means for cutting off the power supply of the emitting apparatus coupled to presence detection means in the open field area of the emitting apparatus. In particular, these detection means may be of the spot type in particular at the level of the doors passages or still they may consist of volumetric detectors.

The invention claimed is:

1. A device for signaling the status of an in-outside radio-electric emitting apparatus with an X-ray tube, the device comprising:
    a first portion connected to said emitting apparatus, and including:
    a current measurer configured to measure a current provided to said emitting apparatus,
    a processor configured to determine a status of said emitting apparatus according to the measured current, the status being one of shut-off, in standby or in use, and
    a transmitter configured to transmit the determined status toward a second portion; and
    the second portion including a status signaler configured to signal the determined status of the emitting apparatus detected by said first portion,
    wherein the status signaler is configured to provide the determined status by at least one of an audible signal, a luminous signal, and a message display, and
    wherein the processor determines the status according to a first low threshold, the first low threshold being lower than a minimum current demand when the emitting apparatus is in standby, and a second high threshold, the second high threshold being lower than the minimum current demand of the emitting apparatus in use.

2. The signaling device according to claim 1, further comprising:
    a first casing and a second casing,
    wherein the first and second portions are positioned remote from each other and are housed, respectively, in the first and second casings; and
    said transmitter including a wireless link.

3. The signaling device according to claim 2, wherein the link between the first and second portions is encoded in order to avoid pairing errors.

4. The signaling device according to claim 1, wherein the current measurer comprises a current clamp meter configured to measure an intensity of the current required by the emitting apparatus.

5. The signaling device according to claim 1, wherein the processor enables self-learning of the first low threshold and the second high threshold during, respectively, the first setting in standby mode and the first setting in operation of the emitting apparatus.

6. The signaling device according to claim 1, wherein the processor comprises a memory including pre-recorded the first low threshold and the second high low threshold according to power consumption of the emitting apparatuses.

7. The signaling device according to claim 1, wherein the first portion includes a power cut off configured to cut off the power supply of the emitting apparatus coupled to a presence detector in an open field area of the emitting apparatus.

8. A set including a central unit configured to receive a signal emitted by a first portion of a first signaling device and by a first portion of a second signaling device, each of the first and second signaling devices configured to signal a respective status of a respective in-outside radio-electric emitting apparatus with an X-ray tube, each of the signaling devices comprising:
    the first portion connected to said emitting apparatus, and including:
    a current measurer configured to measure a current provided to said emitting apparatus,
    a processor configured to determine the status of said respective emitting apparatus according to the measured current, the status being one of shut-off, in standby or in use, and
    a transmitter configured to transmit the determined status toward a second portion; and
    the second portion configured to signal the determined status of the respective emitting apparatus detected by said first portion to the central unit,
    the central unit comprising a status signaler configured to provide the determined status by at least one of an audible signal, a luminous signal, and a message display; and
    wherein the processor determines the status according to a first low threshold, the first low threshold being lower than a minimum current demand when the emitting apparatus is in standby, and a second high threshold, the second high threshold being lower than the minimum current demand of the emitting apparatus in use.

9. The signaling device of claim 1, wherein the current mesaurer is connected to a power cable of said emitting apparatus.

* * * * *